United States Patent
Dangond et al.

(10) Patent No.: US 11,576,757 B1
(45) Date of Patent: Feb. 14, 2023

(54) DENTAL BRIDGE FITTING SYSTEM

(71) Applicants: Victor Dangond, Weeki Wachee, FL (US); Rusia Dangond, Weeki Wachee, FL (US)

(72) Inventors: Victor Dangond, Weeki Wachee, FL (US); Rusia Dangond, Weeki Wachee, FL (US)

( * ) Notice: Subject to any disclaimer, the term of this patent is extended or adjusted under 35 U.S.C. 154(b) by 639 days.

(21) Appl. No.: 16/666,663

(22) Filed: Oct. 29, 2019

(51) Int. Cl.
| | |
|---|---|
| *A61B 5/00* | (2006.01) |
| *A61C 19/04* | (2006.01) |
| *A61C 9/00* | (2006.01) |
| *A61B 1/24* | (2006.01) |
| *A61B 1/045* | (2006.01) |
| *A61B 1/00* | (2006.01) |
| *A61B 1/06* | (2006.01) |

(52) U.S. Cl.
CPC ........ *A61C 9/0053* (2013.01); *A61B 1/00045* (2013.01); *A61B 1/00114* (2013.01); *A61B 1/045* (2013.01); *A61B 1/063* (2013.01); *A61B 1/24* (2013.01); *A61B 5/0088* (2013.01)

(58) Field of Classification Search
CPC .............. A61C 9/0053; A61B 1/00045; A61B 1/00114; A61B 1/045; A61B 1/063; A61B 1/24; A61B 5/0088; A61B 18/24
See application file for complete search history.

(56) References Cited

U.S. PATENT DOCUMENTS

| | | | |
|---|---|---|---|
| 5,011,405 A | | 4/1991 | Lemchen |
| 5,051,823 A | | 9/1991 | Cooper |
| 5,082,007 A | * | 1/1992 | Adell ................ A63B 71/085 128/862 |
| 5,605,459 A | | 2/1997 | Kuroda |
| D399,961 S | | 10/1998 | Nikoderm |
| 6,663,386 B1 | | 12/2003 | Moelsgaard |
| 9,408,673 B2 | | 8/2016 | Monty |
| 10,238,476 B2 | | 3/2019 | Karazivan |
| 2013/0298916 A1 | * | 11/2013 | Alvarez ................ A61C 5/90 264/16 |
| 2015/0305669 A1 | * | 10/2015 | Hultgren ............... A61C 19/05 433/215 |
| 2017/0215997 A1 | * | 8/2017 | Martin ................. A61B 5/6835 |
| 2017/0251954 A1 | * | 9/2017 | Lotan ................... A61B 5/0088 |
| 2018/0078334 A1 | * | 3/2018 | Lotan ................... A61C 19/04 |
| 2019/0365237 A1 | * | 12/2019 | Lee ..................... H04N 5/23299 |
| 2020/0146790 A1 | * | 5/2020 | Marshall .............. A61B 5/0088 |
| 2020/0281701 A1 | * | 9/2020 | Kim ..................... A61B 8/4477 |
| 2021/0236389 A1 | * | 8/2021 | Yang ...................... C04B 35/48 |
| 2022/0165089 A1 | * | 5/2022 | Mochizuki ........... G06V 40/166 |

FOREIGN PATENT DOCUMENTS

EP  0438353  7/1991

* cited by examiner

*Primary Examiner* — Howard D Brown, Jr.
(74) *Attorney, Agent, or Firm* — Kyle A. Fletcher, Esq.

(57) ABSTRACT

The dental bridge fitting system is a medical device. The dental bridge fitting system is configured for use in measuring the oral surface contours of a patient. The measurements taken by the dental bridge fitting system allow for the fabrication of a dental prosthetic device, such as a bridge, that fits flush on the oral surface that was measured by the dental bridge fitting system. The dental bridge fitting system comprises a mouthpiece, a plurality of capture devices, an image processor, and a master processor. The mouthpiece contains the plurality of capture devices. The plurality of capture devices, the image processor, and the master processor are electrically interconnected.

17 Claims, 5 Drawing Sheets

DENTAL BRIDGE FITTING SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including surgical instruments, more specifically, a surgical device for applying and receiving electromagnetic radiation to a body. (A61B18/24)

SUMMARY OF INVENTION

The dental bridge fitting system is a medical device. The dental bridge fitting system is configured for use in measuring the oral surface contours of a patient. The measurements taken by the dental bridge fitting system allow for the fabrication of a dental prosthetic device, such as a bridge, that fits flush on the oral surface that was measured by the dental bridge fitting system. The dental bridge fitting system comprises a mouthpiece, a plurality of capture devices, an image processor, and a master processor. The mouthpiece contains the plurality of capture devices. The plurality of capture devices, the image processor, and the master processor are electrically interconnected.

These together with additional objects, features and advantages of the dental bridge fitting system will be readily apparent to those of ordinary skill in the art upon reading the following detailed description of the presently preferred, but nonetheless illustrative, embodiments when taken in conjunction with the accompanying drawings.

In this respect, before explaining the current embodiments of the dental bridge fitting system in detail, it is to be understood that the dental bridge fitting system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the dental bridge fitting system.

It is therefore important that the claims be regarded as including such equivalent construction insofar as they do not depart from the spirit and scope of the dental bridge fitting system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

The dental bridge fitting system is a medical device. The dental bridge fitting system is configured for use in measuring the oral surface contours of a patient. The measurements taken by the dental bridge fitting system allow for the fabrication of a dental prosthetic device, such as a bridge, that fits flush on the oral surface that was measured by the dental bridge fitting system. The dental bridge fitting system comprises a mouthpiece, a plurality of capture devices, an image processor, and a master processor. The mouthpiece contains the plurality of capture devices. The plurality of capture devices, the image processor, and the master processor are electrically interconnected.

SPECIFICATION

Figure 1:
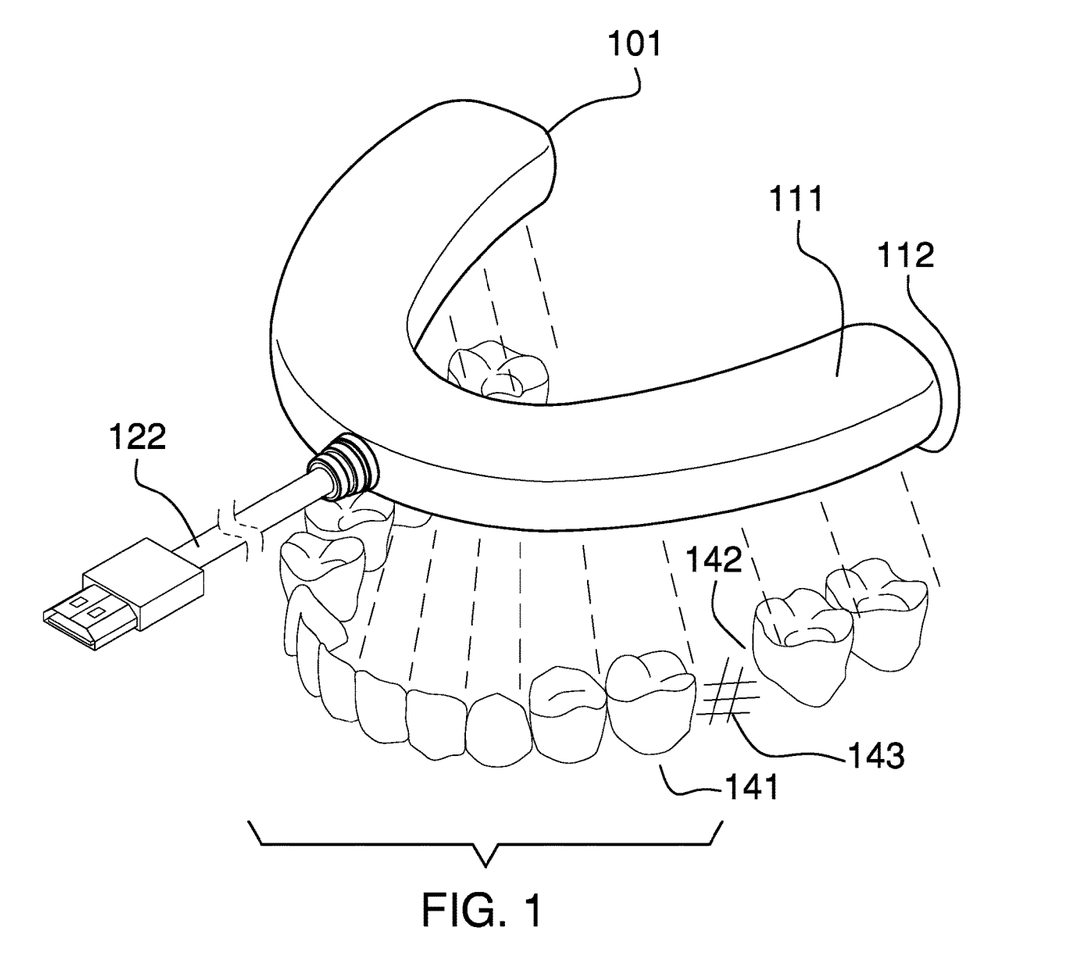
FIG. 1 is a perspective in-use view of an embodiment of the disclosure.
Figure 2:
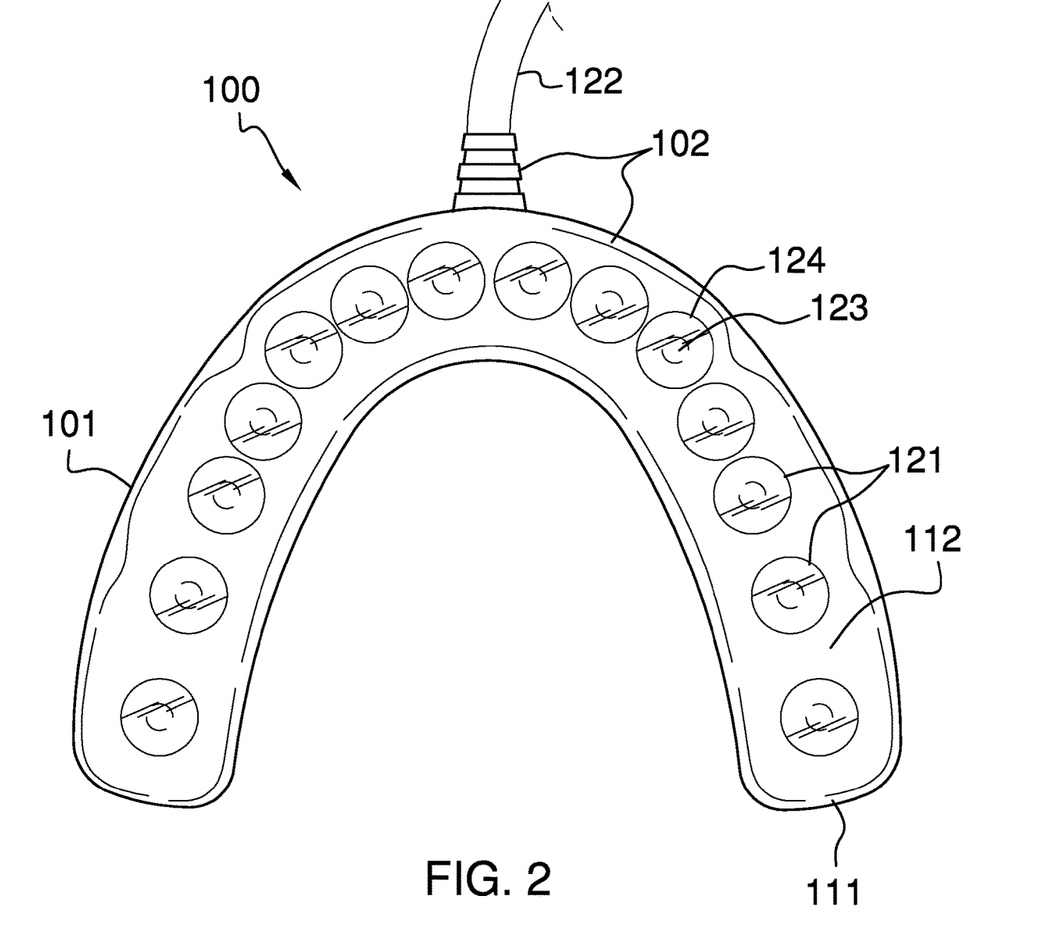
FIG. 2 is a bottom view of an embodiment of the disclosure.
Figure 3:
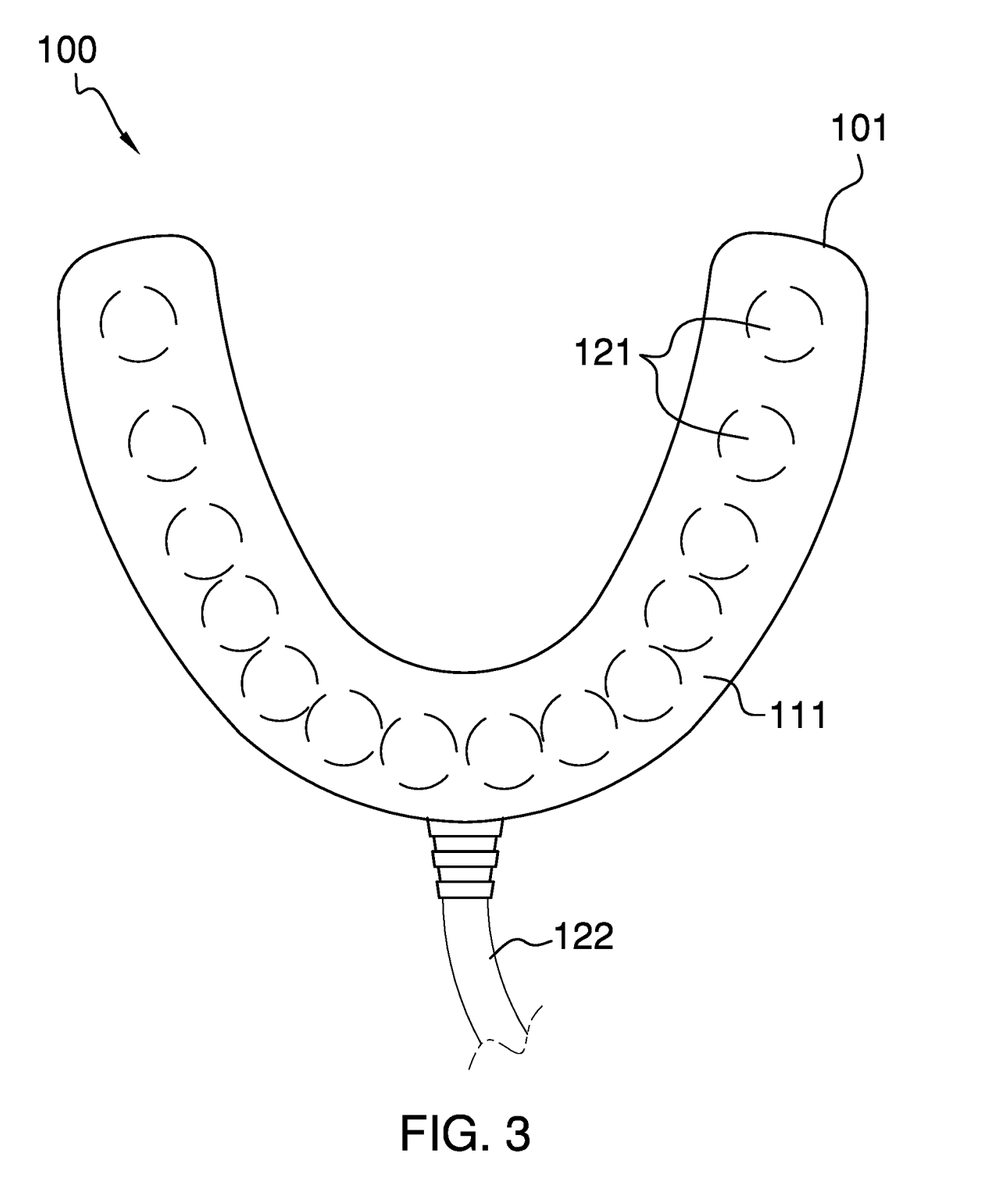
FIG. 3 is a top view of an embodiment of the disclosure.
Figure 4:
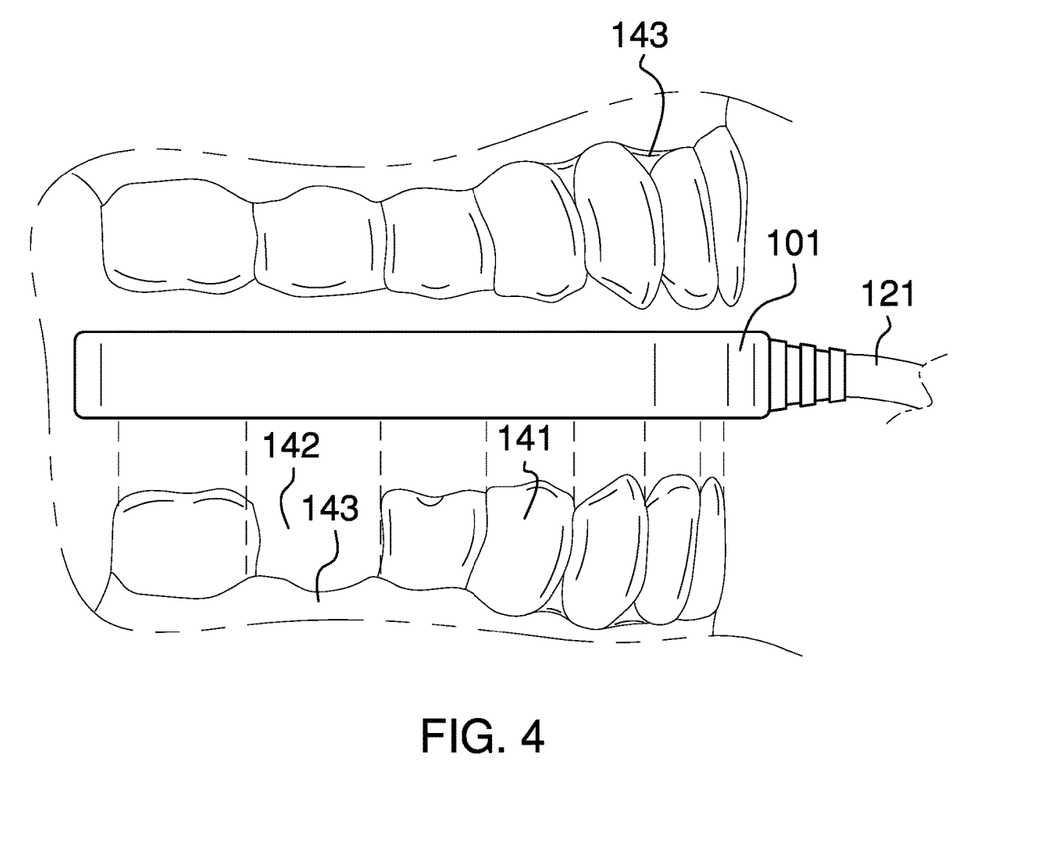
FIG. 4 is a side in-use view of an embodiment of the disclosure.
Figure 5:
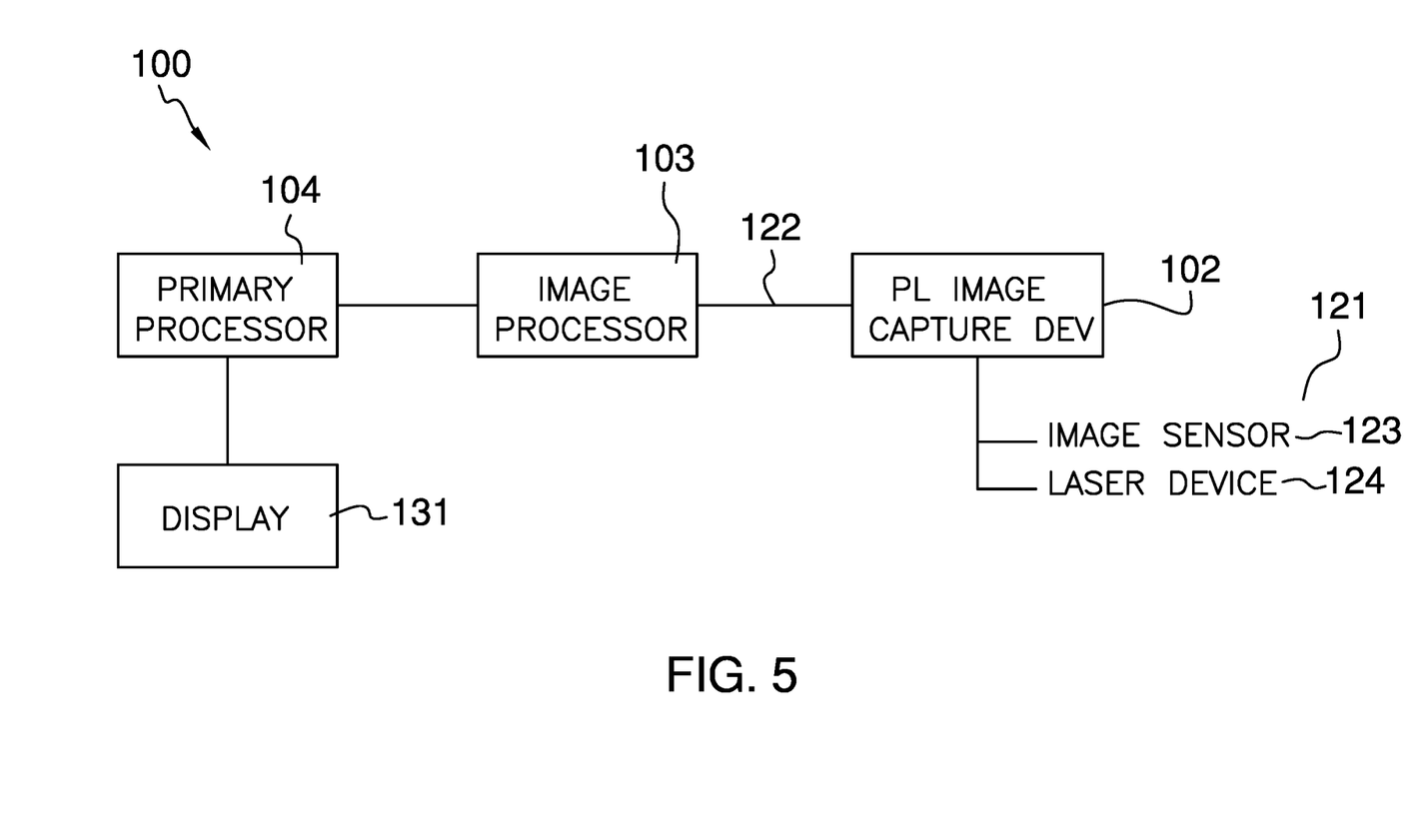
FIG. 5 is a block diagram or schematic view of an embodiment of the disclosure.

Detailed reference will now be made to one or more potential embodiments of the disclosure, which are illustrated in FIGS. 1 through 5.

The dental bridge fitting system 100 (hereinafter invention) is a medical device. The invention 100 is configured for use in measuring the oral surface 143 contours of a patient. The measurements taken by the invention 100 allow for the fabrication of a dental prosthetic device, such as a bridge, that fits flush on the oral surface 143 that was measured by the invention 100. The invention 100 comprises a mouthpiece 101, a plurality of capture devices 102, an image processor 103, and a master processor 104. The mouthpiece 101 contains the plurality of capture devices 102. The plurality of capture devices 102, the image processor 103, and the master processor 104 are electrically interconnected.

The oral surface 143 refers to the portion of the gums of a mouth that are visible between the diastema 142 of the specific dentition 141 of the patient. The dentition 141 is defined elsewhere in this disclosure. The diastema 142 is defined elsewhere in this disclosure.

The mouthpiece 101 is a semi-rigid structure with an elastic nature, which is adapted to fit different size dentitions. The mouthpiece 101 contains the plurality of capture devices 102. The mouthpiece 101 is a disk-shaped structure. The mouthpiece 101 is geometrically similar to the dental arch of the patient such that the mouthpiece 101 follows and fits between the dentition 141 of the mandible and the dentition 141 of the maxilla. The mouthpiece 101 holds the plurality of capture devices 102 in a fixed position when the mouthpiece 101 is held between the dentitions 141 of the mandible and the maxilla. The mouthpiece 101 holds each of the plurality of capture devices 102 such that each individual capture device 121 selected from the plurality of capture devices 102 is positioned over a tooth or diastema 142 selected from a dentition 141 selected from the group consisting of the dentition 141 of the mandible and the dentition 141 of the maxilla. The mouthpiece 101 comprises a base disk 111 and a transparent pan 112.

The base disk 111 is a disk-shaped structure. The base disk 111 is a semi-rigid structure. The congruent ends of the disk-shaped structure of the base disk 111 is roughly shaped to follow the contour of the dental arch of the dentitions 141 of the mandible and the maxilla. Each of the plurality of capture devices 102 mounts on the base disk 111 such that each capture device selected from the plurality of capture devices 102 aligns with a tooth or a diastema 142 selected from a dentition 141 selected from the group consisting of the dentition 141 of the mandible and the dentition 141 of the maxilla. The reversal of the orientation of the base disk 111 changes the selection of the dentition 141 selected from the group consisting of the dentition 141 of the mandible and the dentition 141 of the maxilla that is aligned with the plurality of capture devices 102.

The transparent pan 112 is a pan-shaped structure. The transparent pan 112 is a semi-rigid structure. The congruent ends of the pan-shaped structure of the transparent pan 112 is roughly shaped to follow the contour of the dental arch of the dentitions 141 of the mandible and the maxilla. The transparent pan 112 is sized such that the plurality of capture devices 102 fits within the hollow pan shaped structure of the transparent pan 112. The transparent pan 112 attaches to the base disk 111 such that the plurality of capture devices 102 are enclosed between the base disk 111 and the transparent pan 112.

The transparent pan 112 is a transparent structure. The transparent structure of the transparent pan 112 allows for the monochromatic electromagnetic radiation to escape the plurality of capture devices 102 after generation and allows the monochromatic electromagnetic radiation to be captured by the plurality of capture devices 102 after the monochromatic electromagnetic radiation has been reflected.

Each of the plurality of capture devices 102 is an image capture device. Each of the plurality of capture devices 102 generates a monochromatic electromagnetic radiation. Each of the plurality of capture devices 102 captures a reflection of the generated monochromatic electromagnetic radiation and converts the captured monochromatic electromagnetic radiation into electrical signals that are transmitted to the image processor 103. The plurality of capture devices 102 comprises a collection of individual capture devices 121 and a communication link 122.

The plurality of capture devices 102 comprises 16 individual capture device 121. Each individual capture device 121 is an electrical device. The image processor 103 monitors and controls the operation of the individual capture devices 121. Each individual capture device 121 generates the monochromatic electromagnetic radiation used to map the dentition 141 of the patient. The individual capture device 121 captures and converts the reflection of the generated monochromatic electromagnetic radiation into electrical signals that are transmitted to the image processor 103 for further processing. The image processor 103 independently controls the operation of each individual capture device 121 selected from the plurality of capture devices 102.

Each individual capture device 121 comprises an individual image sensor 123 and an individual laser device 124.

The individual image sensor 123 is a camera that physically captures the reflected monochromatic electromagnetic radiation and converts the captured monochromatic electromagnetic radiation into an electrical signal that is transmitted to the image processor 103.

The individual laser device 124 is an electrical circuit. The image processor 103 controls the operation of the individual laser device 124. The individual laser device 124 generates a monochromatic electromagnetic radiation. The individual laser device 124 transmits the monochromatic electromagnetic radiation through the transparent pan 112 of the mouthpiece 101 toward the selected dentition 141 of the patient.

The communication link 122 is an electric cable that electrically connects each of the plurality of capture devices 102 to the image processor 103. The communication link 122 transmits the electrical signals between the image processor 103 and each of the plurality of capture devices 102.

The image processor 103 is an electrical device. The image processor 103 is a programmable device. The image processor 103 receives the electrical signals generated by each individual capture device 121 selected from the plurality of capture devices 102. The image processor 103 processes the electrical signals received from each individual capture device 121 selected from the plurality of capture devices 102 into an individual data file. The image processor 103 transmits each individual data file to the master processor 104.

The master processor 104 is an electrical device. The master processor 104 is a programmable device. The master processor 104 receives each individual data file containing the images captured by each individual capture device 121 selected from the plurality of capture devices 102. The master processor 104 transforms the data contained in the individual data file into a data structure that provides the targeted oral surface 143 contours necessary to allow a technician to ensure that the dental prosthetic device will fit flush within the mouth of a patient. The data processing methods and techniques necessary to make these calculations are well-known and documented in the electrical arts. The master processor 104 further comprises a display 131.

The display 131 is an electrical device. The display 131 forms a visual interface that visually displays the information about the targeted oral surface 143 contours necessary to allow a technician to ensure that the dental prosthetic device will fit flush within the mouth of a patient.

The following definitions were used in this disclosure:

Cable: As used in this disclosure, a cable is a collection of one or more insulated wires covered by a protective casing that is used for transmitting electricity or telecommunication signals.

Camera: As used in this disclosure, a camera is a sensor that converts light into electric signals that encode and records the spatial orientation of the captured light in a manner that reproduces the images seen by a human eye.

Communication Link: As used in this disclosure, a communication link refers to the structured exchange of data between two objects.

Dental Arch: As used in this disclosure, the dental arch refers to the curvature formed by the dentition. There are two dental arches in a person that are commonly referred to as the superior dental arch and the inferior dental arch.

Dentition: As used in this disclosure, a dentition refers to a set of teeth and a set of descriptive characteristics of the set of teeth especially with regard to their number, kind, arrangement, and condition. Mandible: As used in this disclosure, the mandible is the lower jaw bone of a human being.

Diastema: As used in this disclosure, a diastema is the space between two teeth.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Form Factor: As used in this disclosure, the term form factor refers to the size and shape of an object.

Field of View: As used in this disclosure, a field of view refers to one or more angles that delimits an area from which electromagnetic radiation will be sensed by a person or an image sensor.

Flush: As used in this disclosure, the term flush is used to describe the alignment of a first surface and a second surface on a single plane.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Image: As used in this disclosure, an image is an optical representation or reproduction of an indicia or of the appearance of something or someone.

Image Sensor: As used in this disclosure, an image sensor receives light from the exterior of the image sensor and converts the received light into a digital representation of sufficient detail to allow a logic module to create and display a visual reproduction of the source of the captured light.

Laser: As used in this disclosure, a laser is an electrical device used to generate monochromatic electromagnetic radiation. By monochromatic is meant that the generated photons all have the same wavelength.

Logic Module: As used in this disclosure, a logic module is a readily and commercially available electrical device that accepts digital and analog inputs, processes the digital and analog inputs according to previously specified logical processes and provides the results of these previously specified logical processes as digital or analog outputs. The disclosure allows, but does not assume, that the logic module is programmable.

Mandibular: As used in this disclosure, mandibular means pertaining or related to the mandible.

Maxilla: As used in this disclosure, the maxilla is the upper jaw bone of a human being.

Maxillary: As used in this disclosure, maxillary means pertaining or related to the maxilla.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different.

Patient: As used in this disclosure, a patient is a person who is designated to receive a medical treatment, therapy or service. The term patient may be extended to an animal when used within the context of the animal receiving veterinary treatment or services.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Roughly: As used in this disclosure, roughly refers to a comparison between two objects. Roughly means that the difference between one or more parameters of the two compared objects are not significantly different.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A dental bridge fitting system comprising
a mouthpiece, a plurality of capture devices, an image processor, and a master processor;
wherein the mouthpiece contains the plurality of capture devices;
wherein the plurality of capture devices, the image processor, and the master processor are electrically interconnected;
wherein the dental bridge fitting system is a medical device;
wherein the dental bridge fitting system is configured for use in measuring an oral surface contour;
wherein the mouthpiece is a semi-rigid structure with an elastic nature;
wherein the mouthpiece is a disk-shaped structure;
wherein the mouthpiece is adapted to be geometrically similar to a dental arch;
wherein the mouthpiece holds the plurality of capture devices in a fixed position;
wherein the mouthpiece holds each of the plurality of capture devices such that each individual capture device selected from the plurality of capture devices is positioned over a tooth or diastema selected from a dentition selected from the group consisting of the dentition of the mandible and the dentition of the maxilla;
wherein each of the plurality of capture devices is an image capture device;
wherein each of the plurality of capture devices generates a monochromatic electromagnetic radiation;
wherein each of the plurality of capture devices captures a reflection of the generated monochromatic electromagnetic radiation and converts the captured monochromatic electromagnetic radiation into electrical signals that are transmitted to the image processor.

2. The dental bridge fitting system according to claim 1
wherein the image processor is an electrical device;
wherein the image processor is a programmable device;
wherein the image processor receives the electrical signals generated by each individual capture device selected from the plurality of capture devices;
wherein the image processor processes the electrical signals received from each individual capture device selected from the plurality of capture devices into an individual data file;
wherein the image processor transmits each individual data file to the master processor.

3. The dental bridge fitting system according to claim 2
wherein the master processor is an electrical device;
wherein the master processor is a programmable device;
wherein the master processor receives each individual data file containing the images captured by each individual capture device selected from the plurality of capture devices;
wherein the master processor transforms the data contained in the individual data file into a data structure that provides the targeted oral surface contours.

4. The dental bridge fitting system according to claim 3
wherein the mouthpiece comprises a base disk and a transparent pan;
wherein the transparent pan attaches to the base disk.

5. The dental bridge fitting system according to claim 4
wherein the plurality of capture devices comprises a collection of individual capture devices and a communication link;
wherein the communication link is an electric cable that electrically connects each of the plurality of capture devices to the image processor;
wherein the communication link transmits the electrical signals between the image processor and each of the plurality of capture devices.

6. The dental bridge fitting system according to claim 5
wherein the master processor further comprises a display;
wherein the display is an electrical device;
wherein the display forms a visual interface that visually displays the information about the targeted oral surface contours.

7. The dental bridge fitting system according to claim 6
wherein the base disk is a disk-shaped structure;
wherein the base disk is a semi-rigid structure;
wherein the congruent ends of the disk-shaped structure of the base disk are roughly shaped to follow the contour of a dental arch;
wherein each of the plurality of capture devices mounts on the base disk such that each capture device selected from the plurality of capture devices aligns with a tooth or a diastema selected from a dentition.

8. The dental bridge fitting system according to claim 7
wherein the reversal of the orientation of the base disk changes the selection of the dentition selected from the group consisting of the dentition of the mandible and the dentition of the maxilla that is aligned with the plurality of capture devices.

9. The dental bridge fitting system according to claim 8
wherein the transparent pan is a pan-shaped structure;
wherein the transparent pan is a semi-rigid structure;
wherein the transparent pan is a transparent structure;
wherein the congruent ends of the pan-shaped structure of the transparent pan are roughly shaped to follow the contour of the dental arch.

10. The dental bridge fitting system according to claim 9
wherein the transparent pan is sized such that the plurality of capture devices fits within the hollow pan shaped structure of the transparent pan.

11. The dental bridge fitting system according to claim 10
wherein the transparent pan attaches to the base disk such that the plurality of capture devices are enclosed between the base disk and the transparent pan.

12. The dental bridge fitting system according to claim 11
wherein each individual capture device is an electrical device;
wherein the image processor monitors and controls the operation of the individual capture devices;
wherein each individual capture device generates the monochromatic electromagnetic radiation;
wherein the individual capture device captures and converts the reflection of the generated monochromatic electromagnetic radiation into electrical signals that are transmitted to the image processor.

13. The dental bridge fitting system according to claim 12
wherein the image processor independently controls the operation of each individual capture device selected from the plurality of capture devices.

14. The dental bridge fitting system according to claim 13
wherein the plurality of capture devices comprises 16 individual capture devices.

15. The dental bridge fitting system according to claim 14
wherein each individual capture device comprises an individual image sensor and an individual laser device;
wherein the individual laser device generates the monochromatic electromagnetic radiation;
wherein the individual image sensor is a camera.

16. The dental bridge fitting system according to claim 15 wherein the individual image sensor physically captures the reflected monochromatic electromagnetic radiation and converts the captured monochromatic electromagnetic radiation into an electrical signal that is transmitted to the image processor.

17. The dental bridge fitting system according to claim 16
wherein the individual laser device is an electrical circuit;
wherein the image processor controls the operation of the individual laser device;
wherein the individual laser device transmits the monochromatic electromagnetic radiation through the transparent pan of the mouthpiece.

\* \* \* \* \*